United States Patent [19]

Carpenter

[11] Patent Number: 5,058,439
[45] Date of Patent: Oct. 22, 1991

[54] UT SOCKET ASSEMBLY

[75] Inventor: Michael S. Carpenter, Forest, Va.

[73] Assignee: The Babcock & Wilcox Company, New Orleans, La.

[21] Appl. No.: 534,104

[22] Filed: Jun. 6, 1990

[51] Int. Cl.⁵ .................. G01L 5/24; G01N 29/00
[52] U.S. Cl. .................. 73/862.21; 73/581; 73/761
[58] Field of Search ........... 73/761, 778, 581, 862.21, 73/862.23

[56] References Cited

U.S. PATENT DOCUMENTS 3,969,960  7/1976  Pagano ................. 73/862.23 X
4,625,554  12/1986  Lanzoni ................ 73/862.21 X

FOREIGN PATENT DOCUMENTS 2037430  7/1980  United Kingdom ............ 73/761

*Primary Examiner*—Charles A. Ruehl
*Attorney, Agent, or Firm*—Robert J. Edwards; D. Neil LaHaye

[57] ABSTRACT

An ultrasonic transducer socket assembly for simultaneously tightening a bolt and measuring bolt load. A pole adaptor rigidly attached to a driving socket for engaging and driving a bolt has a stationary cylinder mounted therein. A second cylinder rotatably and slidably received in the stationary cylinder has an ultrasonic transducer pivotally mounted at one end that contacts the bolt to be tightened when the socket is engaged with the bolt. The rotating cylinder and transducer are rotated approximately 180 degrees during engagement of the socket and bolt to smear an even couplant layer between the bolt and transducer to assure consistent measurements of bolt load during tightening.

11 Claims, 1 Drawing Sheet

UT SOCKET ASSEMBLY

BACKGROUND OF THE INVENTION

1. Field of the Invention

The present invention is generally related to an apparatus for determining bolt load and more particularly to an apparatus for remotely monitoring bolt load during and after torquing of the bolt.

2. General Background

In many situations, it is necessary to determine bolt load during assembly operations to insure that parts are joined together within the stress limits for the intended use. In applications where the bolt load is critical, the use of a torque wrench is generally unacceptable due to varying amounts of friction between the bolt and nut, structure, or washer. Devices for indicating the load on a bolt or fastener which applicant is aware of include the following.

U.S. Pat. No. 4,846,001 discloses a piezoelectric sensor permanently coupled to the upper surface of a fastener, contacts electrically engageable with the sensor, and an electronic measurement device responsive to electronic differential signals of the sensor to determine the tensile load of the fastener when stressed longitudinally.

U.S. Pat. Nos. 4,686,859 and 4,676,109 disclose a bolt modified to provide a load indicating fastener wherein a pin is positioned within an axial bore in the bolt so the head of the pin is coplanar with the bolt head. A load indicating device determines bolt load during installation by the use of a differential displacement measurement device to measure the height differential between the upper surfaces of the bolt head and the pin.

U.S. Pat. No. 4,333,351 discloses a method and apparatus for determining the residual tension in a bolt or stud in a joint assembly. A tensioner is used to pull the bolt or stud in a previously tightened joint and an ultrasonic extensometer is used to determine the residual force or tension in the bolt or stud.

U.S. Pat. No. 4,709,182 discloses the use of a vibrator/sensor unit to cause longitudinal oscillation of a bolt to its natural frequency to aid in loosening or tightening the connection to a predetermined value.

U.S. Pat. No. 3,759,090 discloses an ultrasonic extensometer for measuring the elongation of a bolt tightened against a structure. A transducer magnetically coupled to the head of the bolt generates pulse signals into the bolt.

Although the known art provides devices for measuring bolt load, a need exists for a device that is capable of remotely torquing a bolt while simultaneously and consistently indicating the load on the bolt. Much of the known art also requires the use of a modified bolt to determine bolt load. This results in increased costs. Therefore, it can be seen that there is a need for a device that does not need separate torquing and measuring tools and can use the standard bolt intended for the application.

SUMMARY OF THE INVENTION

The present invention solves the aforementioned problem in a straightforward manner. What is provided is a socket assembly that incorporates an ultrasonic transducer/rotating gimbal assembly to remotely monitor bolt load while torquing. As the socket is lowered onto the bolt, the gimbal assembly forces the transducer to rotate and spread a uniform couplant layer between the transducer and the bolt. The assembly has a stationary section and a rotating section. The stationary section is mounted in the socket that engages the flats of the bolt head for torquing the bolt. The rotating section includes a pin that is slidably engaged in a helical slot in the stationary section, a transducer attached to the lower end of the rotating section by means of a gimbal, and a drive pin between the rotating section and gimbal that transfers the rotating motion to the transducer. The rotating section is spring loaded in the stationary section to provide a constant downward force on the transducer. This assures a uniform couplant layer between the bolt and transducer and consistent ultrasonic measurements when determining bolt load.

BRIEF DESCRIPTION OF THE DRAWINGS

For a further understanding of the nature and objects of the present invention reference should be had to the following description, taken in conjunction with the accompanying drawings in which like parts are given like reference numerals, and wherein.

DETAILED DESCRIPTION OF THE PREFERRED EMBODIMENT

Figure 1:
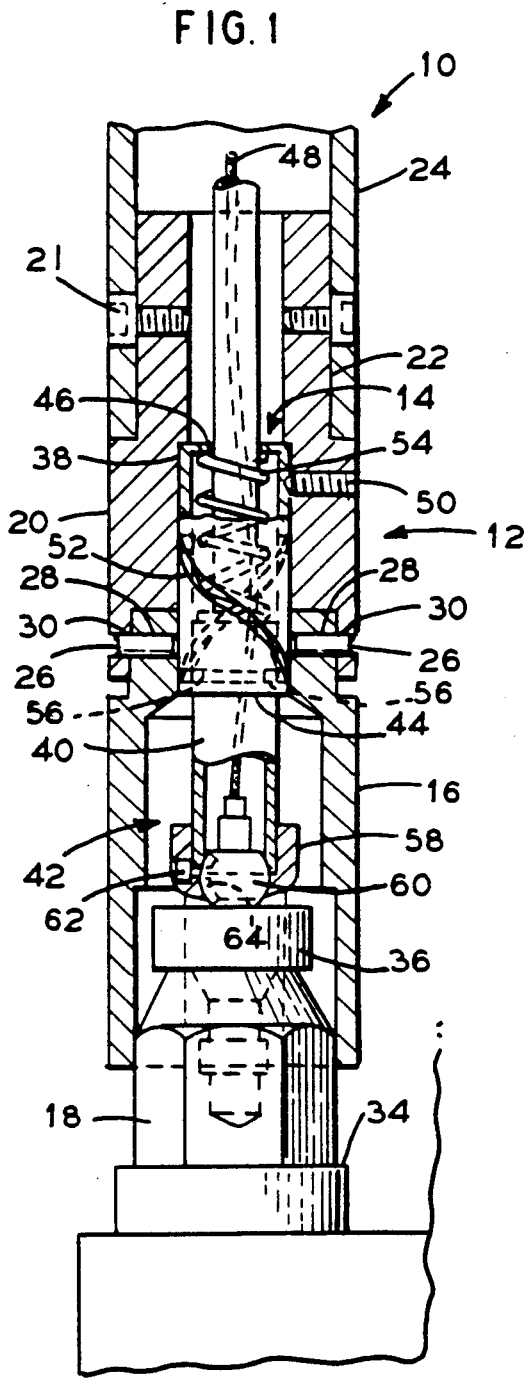
FIG. 1 is a partial sectional view illustrating the invention at initial contact with a bolt.
Figure 2:
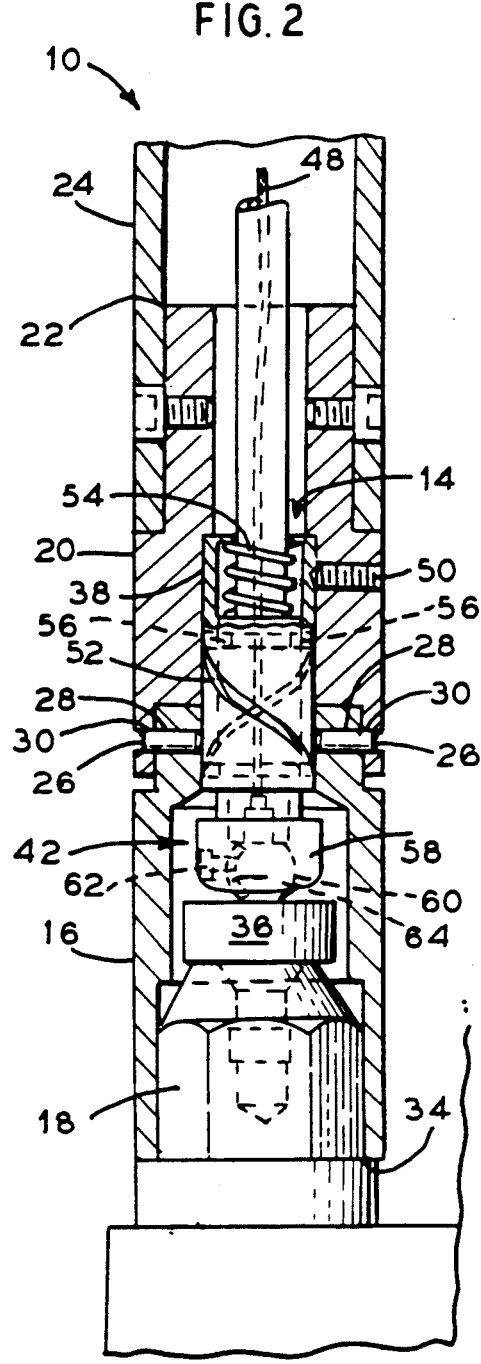
FIG. 2 is a partial sectional view illustrating the invention fully engaged on the bolt head.

Referring to FIG. 1 and 2, it is seen that the invention is generally indicated by the numeral 10. Ultrasonic transducer socket assembly 10 is generally comprised of bolt engaging section 12 and means 14, including a transducer 36, for causing transducer 36 to contact the bolt 18 to be tightened in response to engagement of section 12 with the bolt 18.

Bolt engaging section 12 includes a socket 16 for engaging and driving a bolt (such as a six point socket sized to fit the bolt head 18 of the bolt to be installed) and a pole adaptor 20. Pole adaptor 20 is provided with an upper area 22 having a reduced outer diameter that is received within extension pole 24. Pole adaptor 20 and extension pole 24 are rigidly attached together at upper area 22 by any suitable means such as screws or threaded pins 21. Extension pole 24, like pole adaptor 20, has a longitudinal central bore therethrough and is used with socket 16 for the remote torquing and de-torquing of bolts. Socket 16 is rigidly attached to pole adaptor 20 by pins 26 that are received in radial bores 28, 30 respectively. Socket 16 is provided with an upper portion having a reduced outer diameter whereby it is received within pole adaptor 20 such that bores 28,30 are in coaxial alignment for receiving pins 26. Pins 26 also serve to transfer rotational force to socket 16 from pole adaptor 20. Like pole adaptor 20, socket 16 is provided with a longitudinal bore therethrough.

Means 14, including a transducer 36, is mounted in the longitudinal bores of socket 16 and pole adaptor 20 for causing transducer 36 to contact bolt head 18 at a constant force in response to engagement of socket 16 with bolt head 18. Transducer 36 is used to measure bolt load during tightening thereof. Means 14 is comprised of stationary cylinder 38, rotating cylinder 40 and gimbal assembly 42. Stationary cylinder 38 is a hollow cylinder having a first open end 44 and a second end 46 that is provided with an opening to allow rotating cylinder 40 and transducer cable 48 to pass therethrough. Stationary cylinder 38 is rigidly mounted in the longitudinal bore of pole adaptor 20 by the use of set screws 50 so as to be coaxial with pole adaptor 20. Stationary cylinder 38 is provided with helical slot 52 to be explained below. Rotating cylinder 40 is slidably and rotatably received within stationary cylinder 38. Spring 54 biases cylinder 40 outward of cylinder 38 towards the open end of socket 16 and away from pole adaptor 20 in its first normal extended position illustrated in FIG. 1. Pins 56 provided on cylinder 40 that extend radially outward therefrom are received in helical slot 52. Pins 56 serve to prevent cylinder 40 from being forced completely out of stationary cylinder 38 by spring 54. During initial engagement of socket 16 with bolt head 18, transducer 36 contacts bolt head 18 as seen in FIG. 1. When socket 16 is fully engaged with bolt head 18 as seen in FIG. 2, rotating cylinder 40 is forced into its second retracted position inside stationary cylinder 38 against the pressure of spring 54. During this retraction the riding of pin 56 in helical slot 52 causes rotating cylinder 40, gimbal 42, and transducer 36 to rotate approximately 180 degrees as socket 16 is moved onto bolt head 18. Enough longitudinal travel is provided between stationary cylinder 38 and rotating cylinder 40 so that socket 16 hard stops on the shoulder 34 of bolt head 18 before rotating cylinder 40 runs out of travel in stationary cylinder 38. This results in transducer 36 having a constant bearing pressure against bolt head 18 regardless of the pressure of socket 16 on shoulder 34 during torquing operations. Gimbal assembly 42 allows pivoting of socket assembly 10 with transducer 36 flat against the top of bolt head 18 for accurate measurements. Gimbal assembly 42 is formed from cap 58 and ball 60. Cap 58 is rigidly attached to rotating cylinder 40 and ball 60 is rotatably mounted between cap 58 and rotating cylinder 40 to permit flat placement of transducer 36 on bolt head 18. The upper end of transducer 36 extends through ball 60. Rotation of ball 60 and tranducer 36 in conjunction with rotating cylinder 40 is accomplished by the use of set screw 62 that is threaded through cap 58 and rides in slot 64 on the outside circumference of ball 60. Set screw 62 transfers the rotational motion of rotating cylinder 40 to ball 60 during engagement of socket 16 with bolt head 18 while still allowing movement of ball 60 within a different plane in cap 58.

In operation, extension pole 24 is used to remotely position ultrasonic transducer socket assembly 10 and cause socket 16 to engage bolt head 18. As socket 16 is pushed onto bolt head 18, pin 56 causes rotating cylinder 40 to rotate approximately 180 degrees as transducer 36 contacts bolt head 18 and rotating cylinder 40 is forced against the pressure of spring 54 from its first normal extended position to its second retracted position inside stationary cylinder 38. Causing rotation of transducer 36 is important in applications where ultrasonic testing to determine bolt load is done in or out of water because a couplant is used between the bolt and transducer to insure transmission of the ultrasonic signals between the bolt and transducer. The rotation of the transducer smears the couplant on the bolt head in a uniform layer between the transducer and the bolt head. This assures that measurements are consistent. The pressure of transducer 36 is constant against bolt head 18 throughout the torquing operation due to spring 56. As the bolt is tightened, measurements of changes in bolt length by the use of ultrasonic transducer 36 in a manner known in the industry are used to simultaneously determine bolt load. Signals between transducer 36 and instrumentation not shown are transmitted through transducer cable 48. It should be understood that the terms stationary and rotating with regard to cylinders 38,40 are used to indicate their relative movement to each other during engagement of socket 16 onto bolt head 18.

Because many varying and differing embodiments may be made within the scope of the inventive concept herein taught and because many modifications may be made in the embodiment herein detailed in accordance with the descriptive requirement of the law, it is to be understood that the details herein are to be interpreted as illustrative and not in a limiting sense.

I claim:

1. An ultrasonic transducer socket assembly for simultaneously tightening a bolt and remotely measuring bolt load, comprising:
   a. a pole adaptor having a longitudinal bore therethrough;
   b. a socket for engaging and driving a bolt with the socket being rigidly attached to said pole adaptor and having a longitudinal bore therethrough;
   c. an ultrasonic transducer positioned in said socket; and
   d. means attached to said transducer and mounted in the longitudinal bores of said socket and said pole adaptor for causing said transducer to contact the bolt to be tightened at a constant force in response to engagement of said socket with the bolt and to rotate approximately 180 degrees during engagement of said socket with the bolt whereby said transducer is used to measure bolt load.

2. The assembly of claim 1, wherein said contact means comprises:
   a. a stationary cylinder mounted in the longitudinal bore of said pole adaptor; and
   b. a rotating cylinder slidably and rotatably received within said stationary cylinder and having said transducer mounted at one end thereof.

3. The assembly of claim 2, wherein said transducer is pivotally mounted on said rotating cylinder.

4. The assembly of claim 2, further comprising means in said stationary cylinder for biasing said rotating cylinder outward of said stationary cylinder whereby said rotating cylinder is movable between a first normal extended position and a second retracted position.

5. An ultrasonic transducer socket assembly for simultaneously tightening a bolt and measuring bolt load, comprising:
   a. a pole adaptor having a longitudinal bore therethrough;
   b. a socket for engaging and driving a bolt with the socket being rigidly attached to said pole adaptor and having a longitudinal bore therethrough;
   c. an ultrasonic transducer positioned in said socket; and
   d. means mounted in the longitudinal bores of said socket and said pole adaptor for causing said transducer to contact the bolt to be tightened at a constant force in response to engagement of said socket with the bolt and to rotate approximately 180 degrees during engagement of said socket with the bolt whereby said transducer is used to measure bolt load and is pivotally mounted on said contact means.

6. The assembly of claim 5, wherein said contact means comprises:

a. a stationary cylinder mounted in the longitudinal bore of said pole adaptor; and b. a rotating cylinder slidably and rotatably received within said stationary cylinder and having said transducer pivotally mounted at one end thereof.

7. The assembly of claim 6, further comprising means in said stationary cylinder for biasing said rotating cylinder outward of said stationary cylinder whereby said rotating cylinder is movable between a first normal extended position and a second retracted position.

8. An ultrasonic transducer socket assembly for simultaneously tightening a bolt and measuring bolt load, comprising:

a. a pole adaptor having a longitudinal bore therethrough;

b. a socket for engaging and driving a bolt with the socket being rigidly attached to said pole adaptor and having a longitudinal bore therethrough;

c. a stationary cylinder mounted in the longitudinal bore of said pole adaptor;

d. a rotating cylinder slidably and rotatably received within said stationary cylinder so as to be movable between a first normal extended position and a second retracted position; and e. an ultrasonic transducer mounted at one end of said rotating cylinder such that said transducer is in contact with the bolt to be tightened when said socket is engaged with the bolt.

9. The assembly of claim 8, wherein said rotating cylinder is caused to rotate approximately 180 degrees during engagement of said socket with the bolt.

10. The assembly of claim 8, wherein said transducer is pivotally mounted on said rotating cylinder.

11. The assembly of claim 8, further comprising a spring in said stationary cylinder for biasing said rotating cylinder to its first normal extended position.

* * * * *